US010156464B2

(12) United States Patent
Edward et al.

(10) Patent No.: US 10,156,464 B2
(45) Date of Patent: Dec. 18, 2018

(54) FLUID SENSOR

(71) Applicant: M-Flow Technologies Ltd., Abingdon (GB)

(72) Inventors: Giles Edward, Abingdon (GB); Alan Parker, Abingdon (GB); Petr Hajek, Oxford (GB)

(73) Assignee: M-Flow Technologies Ltd, Abingdon (GB)

( * ) Notice: Subject to any disclaimer, the term of this patent is extended or adjusted under 35 U.S.C. 154(b) by 316 days.

(21) Appl. No.: 14/898,255

(22) PCT Filed: Jun. 30, 2014

(86) PCT No.: PCT/GB2014/051981
§ 371 (c)(1),
(2) Date: Dec. 14, 2015

(87) PCT Pub. No.: WO2015/001323
PCT Pub. Date: Jan. 8, 2015

(65) Prior Publication Data
US 2016/0146743 A1    May 26, 2016

(30) Foreign Application Priority Data

Jul. 1, 2013    (GB) .................................. 1311755.1

(51) Int. Cl.
*G01F 1/56*        (2006.01)
*G01F 1/58*        (2006.01)
(Continued)

(52) U.S. Cl.
CPC ................ *G01F 1/56* (2013.01); *G01F 1/582* (2013.01); *G01F 1/586* (2013.01); *G01F 1/66* (2013.01);
(Continued)

(58) Field of Classification Search
CPC . G01F 1/56; G01F 1/582; G01F 1/586; G01F 1/66
See application file for complete search history.

(56) References Cited

U.S. PATENT DOCUMENTS 5,313,216 A * 5/1994 Wang .................... H01Q 9/27
343/700 MS
6,005,527 A * 12/1999 Gomez ................ H01Q 1/1271
343/711
(Continued)

FOREIGN PATENT DOCUMENTS

CN    202383089 U    8/2012
EP    2089694 A1     8/2009
(Continued)

OTHER PUBLICATIONS

Penirschke, Andreas et al., "Microwave Mass Flow Detector for Particulate Solids Based on Spatial Filtering Velocimetry," IEEE Transactions on Microwave Theory and Techniques, vol. 56, No. 12, pp. 3193-3199, IEEE Service Center, Piscataway, N.J. (Dec. 1, 2008).

(Continued)

*Primary Examiner* — Paul West
(74) *Attorney, Agent, or Firm* — Levy & Grandinetti

(57) ABSTRACT

A fluid sensor includes a core defining a fluid flow path, a confinement member located externally of the core, and a patch antenna located between the fluid flow path and the confinement member. The confinement member is configured to confine an electromagnetic field which extends into the fluid flow path. The patch antenna is configured to couple an electrical signal to and/or from the electromagnetic field. The fluid sensor may be configured for measuring the composition and/or flow rate of a fluid and, in particular but (Continued)

not exclusively, for measuring the composition and/or flow rate of mixtures of oil, water and gas.

37 Claims, 11 Drawing Sheets

(51) Int. Cl.
  *G01N 22/00* (2006.01)
  *G01F 1/66* (2006.01)
  *G01F 1/74* (2006.01)
  *G01N 33/28* (2006.01)
(52) U.S. Cl.
  CPC ............... *G01F 1/74* (2013.01); *G01N 22/00* (2013.01); *G01N 33/2823* (2013.01); *G01F 1/58* (2013.01)

(56) References Cited

U.S. PATENT DOCUMENTS

| | | | |
|---|---|---|---|
| 6,915,707 | B2 | 7/2005 | Nyfors et al. |
| 7,015,861 | B2 | 3/2006 | Boyd et al. |
| 2004/0244501 | A1 | 12/2004 | Nyfors et al. |
| 2005/0183514 | A1* | 8/2005 | Huybrechts ............. G01F 1/588 73/861.12 |
| 2008/0087099 | A1 | 4/2008 | Allenberg et al. |
| 2009/0231205 | A1* | 9/2009 | Burke .................. H01Q 9/0407 343/700 MS |
| 2011/0196625 | A1 | 8/2011 | Sheila-Vadde et al. |
| 2012/0111124 | A1 | 5/2012 | Hu |
| 2016/0032062 | A1* | 2/2016 | Clauss .................. C08J 3/2053 523/468 |

FOREIGN PATENT DOCUMENTS

| | | |
|---|---|---|
| EP | 2366980 A2 | 9/2011 |
| GB | 2490685 | 11/2012 |
| JP | 09159623 A * | 6/1997 |
| JP | H09 159623 A | 6/1997 |
| WO | WO 2012/153090 | 11/2012 |

OTHER PUBLICATIONS

International Search Report PCT/ISA/210 for International Application No. PCT/GB2014/051981 dated Aug. 14, 2014.

Written Opinion of the International Searching Authority PCT/ISA/237 for International Application No. PCT/GB2014/051981 dated Aug. 14, 2014.

Search Report for corresponding Great Britain Application No. GB1311755.1 dated Dec. 13, 2013.

* cited by examiner

FLUID SENSOR

CROSS-REFERENCE TO RELATED APPLICATIONS

This is a National Phase of PCT Patent Application No. PCT/GB2014/051981, filed on Jun. 30, 2014, and claims priority to, Great Britain Application No. 1311755.1, filed Jul. 1, 2013, the contents of each of which are hereby incorporated by reference in their entirety.

FIELD

The present invention relates to a fluid sensor for measuring the composition and/or flow rate of a fluid and, in particular but not exclusively, for measuring the composition and/or flow rate of mixtures of oil, water and gas.

BACKGROUND

It is known to measure the composition and/or flow rate of a fluid by passing the fluid through a radio frequency (RF) electromagnetic field and measuring changes in properties of the electromagnetic field. Conventional multiphase meters which are based on this principle typically comprise a base pipe defining a fluid flow path internally thereof and a concentric cylindrical metallic cavity member arranged around the base pipe. The cavity member provides confinement for an electromagnetic field which extends through the base pipe into the fluid flow path. The base pipe is generally transparent to the electromagnetic field and the cavity member is generally metallic. The cavity member generally supports one or more electromagnetic modes. The electromagnetic modes supported by the cavity member depend not only on the geometry of the cavity, but also on the cavity contents including any fluid present in the fluid flow path. Such known multiphase meters are generally used to measure a frequency response of the electromagnetic field. The measured frequency response may include one or more resonant features associated with the one or more electromagnetic modes. The composition and/or flow rate of any fluid present in the fluid flow path may be extracted from characteristics of the resonant features.

The transparent base pipe is typically configured for connection into a metal pipeline. The cross-sectional geometry of the base pipe is generally configured to match the cross-sectional of the metal pipeline. The inner diameter of the cylindrical cavity member is generally selected to be greater than the outer diameter of the metal pipeline. This may ensure that the fundamental frequency of the electromagnetic field within the cavity defined by the cavity member is less than the minimum frequency that can be propagated in the pipeline so as to minimise the loss of electromagnetic energy from the cavity along the pipeline. In known multiphase meters the annular region defined between the outer surface of the base pipe and the inner surface of the cavity member is generally filled with air or water. Examples of such conventional multiphase meters are described in S. Al-Hajeri, S. R. Wylie, R. A. Stuart and A. I. Al-Shamma'a, "An electromagnetic cavity sensor for multiphase measurement in: the oil and gas industry", Journal of Physics: Conference Series 76 (2007) 012007; in S. Al-Hajeri, S. R. Wylie, A. Shaw and A. I. Al-Shamma'a "Real time EM waves monitoring system for oil industry three phase flow measurement", Journal of Physics: Conference Series 178 (2009) 012030; in S. R. Wylie, A. I. Al-Shamma'a, A. Shaw and S. Al-Hajeri, "Electromagnetic cavity sensors for multiphase measurement", Exploration and Production Oil and Gas Review, Volume 9, Issue 1; and in Finnish patent document no. FI834892.

The Applicant's co-pending UK patent application no. 1218956.9 discloses a fluid sensor comprising a core including a base member such as a base pipe which defines a fluid flow path and a filler member such as a polyether ether ketone (PEEK) filler member located externally of the base member. The fluid sensor further comprises a cavity member for confining an electromagnetic field. The cavity member is located externally of the core. The cavity member may be formed on an outer surface of the core.

Known multiphase meters generally use one of two different antenna configurations for coupling energy between an electrical source and an electromagnetic field within the cavity and/or for coupling energy between the electromagnetic field and an electrical receiver: a monopole antenna including a straight conductor which protrudes into the cavity for coupling with the electric field, or a loop antenna including a electrically conductive loop that protrudes into the cavity and which is connected back to ground for coupling with the magnetic field. To provide acceptable performance, conventional monopole and loop antennas generally protrude radially inwardly from the cavity member by several cm's. As such, conventional monopole and loop antennas generally extend into the annular region which exists in conventional multiphase meters between the outer surface of a base pipe and the inner surface of a cavity member as already described above. A passage is generally formed into or through the core so as to accommodate a monopole antenna or a loop antenna. A potable compound, resin or the like is then used to fill or seal any gaps between the monopole or loop antenna and the passage for environmental integrity and/or electrical insulation. However, the use of conventional monopole and loop antennas in this way may compromise structural strength, environmental integrity and/or electrical insulation. This may be a problem when the multiphase meter is to be used in a hostile environment such as a subsea or a downhole environment.

SUMMARY

According to an aspect of the present invention there is provided a fluid sensor comprising:
  a core defining a fluid flow path;
  a confinement member located externally of the core; and
  a patch antenna located between the fluid flow path and the confinement member,
  wherein the confinement member is configured to confine an electromagnetic field which extends into the fluid flow path and the patch antenna is configured to couple an electrical signal to and/or from the electromagnetic field.

The electromagnetic field may comprise a radio frequency (RF) electromagnetic field, a microwave field or a mm-wave field. The electromagnetic field may have a frequency in the range, 1 kHz to 1 THz, 10 kHz to 100 GHz, 100 kHz to 10 GHz, or 1 MHz to 1 GHz.

The confinement member may define a cavity through which the fluid flow path extends.

The fluid sensor may comprise an electrical source. The patch antenna may be configured to couple energy from the electrical signal source to the electromagnetic field.

The fluid sensor may comprise an electrical detector.

The fluid sensor may comprise a controller.

The controller may be configured to determine the contents of the cavity including any fluid present in and/or flowing through the fluid flow path from an electrical signal detected by the electrical detector and a configuration of the cavity.

The controller may be pre-programmed with the configuration of the cavity for this purpose.

The patch antenna may be configured to couple energy from the electromagnetic field to the electrical detector.

The fluid sensor may comprise an electrical signal separation device for separating an electrical signal provided from the electrical source to the patch antenna from an electrical signal provided from the patch antenna to the electrical detector. For example, the fluid sensor may comprise at least one of a splitter, a coupler, a partial reflector, a signal tap, a circulator or the like.

Such a folded fluid sensor geometry may rely on the reflection of electromagnetic radiation within the cavity. Such a folded fluid sensor geometry may simplify the manufacture of the fluid sensor.

The fluid sensor may comprise a further antenna.

The further antenna may comprise a further patch antenna.

The further antenna may comprise an antenna of a kind other than a patch antenna. For example, the further antenna may comprise at least one of a monopole antenna and a loop antenna or the like.

One of the patch antenna and the further antenna may be configured to couple energy from the electrical signal source to the electromagnetic field and the other of the patch antenna and the further antenna may be configured to couple energy from the electromagnetic field to the electrical detector.

Such an unfolded fluid sensor geometry may avoid any requirement for an electrical signal separation device.

The fluid sensor may comprise a plurality of further antennas.

At least one of the further antennas may comprise a patch antenna.

Each of the plurality of further antennas may be configured to couple energy from the electromagnetic field to a respective electrical detector.

Each of the plurality of further antennas may be configured to couple energy from the electromagnetic field to the same electrical detector at different times.

Such a plurality of further antennas may serve to couple energy from different parts of the electromagnetic field or may serve to couple energy from the electromagnetic field along different directions.

The controller may be configured to determine the contents of the cavity including any fluid present in and/or flowing through the fluid flow path from an electrical signal coupled by each further antenna.

The controller may be configured to determine the contents of the cavity including any fluid present in and/or flowing through the fluid flow path from a magnitude of an electrical signal coupled by each further antenna.

The electrical source may comprise an electrical transmitter.

The fluid sensor may be configured such that an electrical signal generated by the electrical transmitter is substantially independent of the configuration of the cavity and/or which is substantially independent of the contents of the cavity including any fluid present in and/or flowing through the fluid flow path.

The fluid sensor may be configured such that an electrical signal generated by the electrical transmitter has a frequency which is substantially independent of the configuration of the cavity and/or which is substantially independent of the contents of the cavity including any fluid present in and/or flowing through the fluid flow path.

The electrical transmitter may be configured to sweep a frequency of the transmitted electrical signal. The electrical detector may be configured to detect an electrical signal as a function of the frequency of the transmitted electrical signal. The electrical transmitter may be a tunable narrowband electrical transmitter. The electrical detector may be a broadband electrical detector i.e. the electrical detector may not be capable of discriminating between different frequencies.

The electrical transmitter may be configured to transmit a broadband electrical signal. The electrical detector may be configured to determine a frequency spectrum of the detected electrical signal.

The controller may be configured to determine a frequency response of the cavity and/or the contents of the cavity including any fluid present in and/or flowing through the fluid flow path from the transmitted electrical signal and/or the detected electrical signal as a function of frequency.

The electrical transmitter may comprise at least one of an oscillator, a frequency source, a signal generator and the like.

The cavity may be a resonant cavity for one or more electromagnetic modes. The one or more electromagnetic modes may depend on the configuration of the cavity and/or on the contents of the cavity including any fluid present in and/or flowing through the fluid flow path. A resonant cavity may provide enhanced measurement sensitivity of a composition and/or flow rate of any fluid present in and/or flowing through the fluid flow path.

The controller may be configured to determine the contents of the cavity including any fluid present in and/or flowing through the fluid flow path from one or more resonant features of the determined frequency response.

The one or more resonant features of the determined frequency response may comprise one or more resonant peaks and/or one or more resonant dips.

The cavity may be a non-resonant cavity. The cavity may be configured so as to at least partially suppress any resonant features existing on the electrical signal detected by the electrical detector. The cavity may be configured so as to at least partially suppress interference effects between a electromagnetic wave transmitted into the cavity and an electromagnetic wave reflected within the cavity. The cavity may be configured so as to at least partially suppress the formation of any significant standing waves within the cavity.

The electrical transmitter may be configured to transmit an electrical signal with a first frequency.

The electrical transmitter may be configured to transmit an electrical signal with a second frequency.

The electrical transmitter may be configured to transmit the first and second frequencies sequentially.

The controller may be configured to determine a difference in phase between a first electrical signal detected by the electrical detector when the first frequency is transmitted and a second electrical signal detected by the electrical detector when the second frequency is transmitted.

The controller may be configured to measure a first phase of an electrical signal detected by the electrical detector when the electrical transmitter transmits the first frequency.

The controller may be configured to measure a second phase of an electrical signal detected by the electrical detector when the electrical transmitter transmits the second frequency.

The controller may be configured to determine a phase difference between the first and second phases.

The controller may be configured to determine a composition and/or flow rate of any fluid present in and/or flowing through the fluid flow path from the determined phase difference.

The controller may be configured to perform an inverse Fourier transform of the determined frequency response so as to provide a time domain trace.

The controller may be configured to use a Frequency Domain Reflectometry (FDR) technique to determine a composition and/or flow rate of any fluid present in and/or flowing through the fluid flow path.

The electrical transmitter may be configured to repeatedly sweep a frequency of the transmitted electrical signal.

The electrical transmitter may be configured to continuously sweep a frequency of the transmitted electrical signal.

The electrical detector may be configured to monitor a frequency of the electrical signal detected as a function of time.

The controller may be configured to determine a time domain trace from the electrical signal detected by the electrical detector as a function of time.

The controller may be configured to determine a time domain trace of each electrical signal coupled by each further antenna.

The controller may be configured to determine the contents of the cavity including any fluid present in and/or flowing through the fluid flow path from a time domain trace of each electrical signal coupled by each further antenna.

The controller may be configured to use a Frequency Modulated Continuous Wave (FMCW) technique to determine the time domain trace.

The controller may be configured to determine a composition and/or flow rate of any fluid present in and/or flowing through the fluid flow path from the time domain trace.

The controller may be configured to determine a composition and/or flow rate of any fluid present in and/or flowing through the fluid flow path from one or more features of the time domain trace.

The controller may be configured to use a time of flight technique to determine a composition and/or flow rate of any fluid present in and/or flowing through the fluid flow path.

The controller may be configured to determine the contents of the cavity including any fluid present in and/or flowing through the fluid flow path using a time of flight technique for each electrical signal coupled by each further antenna.

The electrical transmitter may be configured to generate electrical pulses.

The electrical detector may be configured to detect electrical pulses.

The controller may be configured to use a time of flight technique to determine a composition and/or flow rate of any fluid present in and/or flowing through the fluid flow path from the detected electrical pulses.

The controller may be configured to use a Time Domain Reflectometry (TDR) technique to determine a composition and/or flow rate of any fluid present in and/or flowing through the fluid flow path from the detected electrical pulses.

The electrical source may comprise again element.

The gain element and the cavity defined by the confinement member may together define an oscillator capable of generating one or more resonant oscillator modes. Each oscillator mode may be associated with one or more corresponding resonant features of a frequency spectrum of an electrical signal detected by the electrical detector. In such an arrangement, the frequencies of the resonant oscillator modes may be more sensitive to a composition and/or flow rate of any fluid present in and/or flowing through the fluid flow path than an arrangement in which the cavity defined by the confinement member lies outside or does not form part of a cavity of the oscillator.

The controller may be configured to determine the contents of the cavity defined by the confinement member including any fluid present in and/or flowing through the fluid flow path from the one or more resonant features of a frequency spectrum of the detected signal.

The one or more resonant features of the detected signal may comprise one or more resonant peaks and/or one or more resonant dips in the frequency spectrum of the detected signal.

The gain element may comprise at least one of an amplifier, a gain medium and the like.

The core may be configured to permit transmission of electromagnetic radiation at a frequency of the electromagnetic field.

The core may be configured to be substantially transparent to electromagnetic radiation at a frequency of the electromagnetic field.

The core may comprise a PEEK material.

The core may comprise a glass.

The core may comprise one or more glass fibres.

The confinement member may comprise an electrically conductive material.

The confinement member may comprise a metal.

The confinement member may comprise a composite material.

The confinement member may comprise one or more reinforcing elements embedded within a matrix.

The one or more reinforcing elements may be electrically conductive.

The one or more reinforcing elements may be electrically conductive and the matrix may be electrically insulating.

The one or more reinforcing elements may comprise carbon.

The one or more reinforcing elements may comprise a metal.

The one or more reinforcing elements may comprise a fibre, strand, particle, nanotube or the like.

The one or more reinforcing elements may comprise carbon fibres.

The matrix may comprise a PEEK material.

The matrix may be electrically conductive.

The one or more reinforcing elements may be electrically insulating and the matrix may be electrically conductive.

The patch antenna may be formed on or around the core.

The patch antenna may be located between the core and the confinement member.

The confinement member may be formed on or around the patch antenna.

The confinement member may be formed on or around the core.

The use of such a patch antenna may avoid any requirement to form a passage into or through the core so as to accommodate a monopole antenna or a loop antenna. Furthermore, the use of a patch antenna avoids any requirement to use a potable compound, resin or the like to fill or seal any gaps between a monopole antenna or a loop antenna and a passage formed through the core to accommodate such an antenna. Accordingly, such a fluid sensor is not only simpler to manufacture, but may also provide improved structural strength, improved environmental integrity and/or improved electrical insulation compared with known fluid sensors incorporating a monopole antenna or a loop antenna. Moreover, the use of the patch antenna may allow a thickness of a wall of the core to be selected independently of the antenna geometry. This may provide improved performance and/or may reduce manufacturing complexity and cost.

The use of a patch antenna may provide greater design freedom compared with a monopole or loop antenna. For example, the patch antenna may be configured so that a resonant frequency of the patch antenna is different from, for example greater than, a resonant frequency of an electromagnetic mode of an electromagnetic cavity defined by the confinement member and its contents. The patch antenna may be configured so that the resonant frequency of the patch antenna is sufficiently different from the resonant frequency of a predetermined mode of the cavity so that any changes in the impedance of the antenna are insignificant over the operating frequency range of the fluid sensor which includes the resonant frequency. This may mean that a frequency response measured using the fluid sensor over the operating frequency range of the fluid sensor is essentially independent of the configuration of the patch antenna. This may simplify the interpretation of the frequency response measured using the fluid sensor. Additionally or alternatively, this may improve the accuracy of a measurement of a composition and/or a flow rate of any fluid present in the fluid flow path.

The patch antenna may be at least partially embedded within the core.

The core may comprise a base member which defines the fluid flow path.

The base member may comprise a base pipe.

The patch antenna may be at least partially embedded within the base member.

The patch antenna may be formed on or around the base member.

The patch antenna may be located between the base member and the confinement member.

The core may comprise a base member and a filler member located externally of the base member.

The filler member may be formed on or around the base member.

The patch antenna may be at least partially embedded within the filler member.

The patch antenna may be formed on or around the filler member.

The patch antenna may be located between the filler member and the confinement member.

The confinement member may be formed on or around the filler member.

The patch antenna may comprise an electrically conductive radiating element.

The radiating element may comprise a non-metallic electrically conductive material or substance.

Such a radiating element may be more easily embedded, bonded, adhered or otherwise incorporated with a matrix material compared with a radiating element formed of or comprising a metal. This may provide the fluid sensor with improved structural strength and/or environmental integrity.

The radiating element may comprise one or more electrically conductive particles, fibres, sheets, nanotubes or the like.

The radiating element may comprise carbon.

A radiating element comprising carbon may be readily embedded into a matrix material such as a PEEK matrix material. Such a radiating element may, in particular, form a bond or be compatible with a core and/or confinement member comprising a matrix material such as a PEEK matrix material. This may provide greater structural strength compared with a metal radiating element embedded into or adjacent to a matrix material such as a PEEK matrix material.

The radiating element may comprise a carbon film.

The radiating element may comprise at least one of carbon graphite, carbon nanotubes, carbon nanostructures, graphene and the like. Such carbon materials may have relatively high conductivity when used as a film.

The radiating element may comprise a metallic electrically conductive material or substance.

The patch antenna may comprise an electrically insulating substrate. The substrate may comprise any one or more of the matrix materials of which the core and/or confinement member may comprise. For example, the substrate may comprise a PEEK material. The substrate may comprise at least a portion of the core.

The radiating element may be defined on a first side of the substrate. The radiating element may be formed by coating, printing, painting or otherwise applying an electrically conductive substance to the first side of the substrate.

The patch antenna may comprise an electrically conductive back plane. The back plane may comprise any one or more of the materials of which the radiating element may comprise.

The back plane may be defined on a second side of the substrate opposite to the first side of the substrate. The back plane may be formed by coating, printing, painting or otherwise applying an electrically conductive substance to the second side of the substrate.

The back plane may be defined by the confinement member. For example, the back plane may be defined by an inner surface of the confinement member.

The patch antenna may be configured according to the composition and/or flow rate of any fluid present in the fluid flow path.

The patch antenna may be configured according to the configuration, for example the geometry and/or composition, of the core.

The patch antenna may be configured according to the configuration, for example the geometry of the resonant cavity defined by the confinement member.

The patch antenna may be configured for coupling between the energy source and the electromagnetic field across a predetermined frequency range including a resonant frequency associated with an electromagnetic mode supported by the cavity.

The patch antenna may be configured to provide improved radiation efficiency and/or directionality compared with a monopole antenna or a loop antenna. For example, the patch antenna may be configured so as to transmit radiation along a preferred direction and/or so as to receive radiation from a preferred direction.

The radiating element may define a triangular shape.

The radiating element may define a rectangular or square shape.

The radiating element may define a circular, oval or elliptical shape.

The fluid sensor may comprise an electrical conductor for providing an external electrical connection to the radiating element.

The fluid sensor may comprise an electrical connection between the electrical conductor and the radiating element.

The electrical conductor may comprise an insulated electrical conductor. The electrical conductor may comprise an electrically insulating outer layer.

The electrical conductor may comprise a wire, cable or the like.

The electrical conductor may extend from the radiating element through a east a portion of the core.

The electrical conductor may extend from the radiating element through at least a portion of the confinement member.

The electrical conductor may extend through the substrate of the patch antenna.

The electrical connection between the electrical conductor and the radiating element may be located at or adjacent to one edge or end of the radiating element.

The radiating element may define an edge opposite the electrical connection with the electrical conductor.

The edge may be configured to provide improved radiation efficiency and/or directionality compared with a monopole antenna or a loop antenna. For example, the shape, length and/or orientation of the edge may be selected to provide improved radiation efficiency and/or directionality compared with a monopole antenna or a loop antenna.

The separation between the edge of the radiating element and the electrical connection with the electrical conductor may be selected to provide improved radiation efficiency and/or directionality compared with a monopole antenna or a loop antenna.

The radiating element may change gradually in shape or geometry between the connection with the electrical conductor and the edge opposite the electrical connection with the electrical conductor.

A cross-section of the radiating element may change gradually between the electrical connection with the electrical conductor and the edge.

A width of the radiating element may change gradually between the electrical connection with the electrical conductor and the edge.

A width of the radiating element may increase gradually between the electrical connection with the electrical conductor and the edge. Such a radiating element may provide a gradual change in impedance across the antenna. This may provide improved radiation efficiency compared with a monopole antenna or a loop antenna.

The radiating element may be symmetrical about an axis extending between the electrical connection with the electrical conductor and a mid-point of the edge.

The edge of the radiating element may be aligned axially relative to a longitudinal axis of the fluid sensor.

The edge of the radiating element may be aligned circumferentially relative to a longitudinal axis of the fluid sensor.

The electrical connection with the electrical conductor may be located at the centre of the radiating element.

The patch antenna may be configured for improved impedance matching compared with a monopole or loop antenna.

The patch antenna may be configured for improved impedance matching over a predetermined band of frequencies.

The radiating element may be electrically connected to the back plane. The fluid sensor may comprise a further electrical conductor for this purpose. The further electrical conductor may extend through the substrate.

The further electrical conductor may provide an external electrical connection to the back plane.

The further electrical conductor may be electrically connected to the radiating element. The further electrical conductor may extend between the radiating element and the back plane.

The radiating element may comprise at least a portion that defines a path such as an elongate path.

The path of the radiating element may extend from a connection between the radiating element and the electrical conductor to a connection between the radiating element and the further electrical conductor.

The path may have a spiral or a convoluted configuration.

The connection between the radiating element and the electrical conductor may be located at or adjacent to a first end of the path.

The connection between the radiating element and the further electrical conductor may be located at or adjacent to a second end of the path opposite to the first end of the path.

A separation of adjacent turns of the path may decrease towards a centre of the path. A curvature of the convoluted or spiral path may increase towards a centre of the path.

The radiating element may comprise an inductor antenna.

Such a radiating element may provide improved impedance matching over a predetermined band of frequencies.

It should be understood that one or more of the optional features disclosed in relation to one aspect may apply alone or in any combination in relation to any other aspect.

According to an aspect of the present invention there is provided a method of manufacturing a fluid sensor comprising:

providing a core defining a fluid flow path;

providing a confinement member externally of the core; and providing a patch antenna between the fluid flow path and the confinement member, wherein the confinement member is configured to confine an electromagnetic field which extends into the fluid flow path and the patch antenna is configured for coupling an electrical signal to and/or from the electromagnetic field.

The method may comprise forming the confinement member on or around the core.

The method may comprise forming the confinement member separately from the core and then locating the confinement member on or around the core.

The method may comprise forming the patch antenna on or around the core.

The method may comprise forming the patch antenna separately from the core and then locating the patch antenna on or around the core.

The method may comprise forming the patch antenna between the core and the confinement member.

The method may comprise forming the patch antenna separately from the core and then locating the patch antenna between the core and the confinement member.

The method may comprise forming the confinement member on or around the patch antenna.

The method may comprise forming the confinement member separately from the patch antenna and then locating the confinement member on or around the patch antenna.

The method may comprise at least partially embedding the patch antenna within the core.

The method may comprise defining an electrically conductive radiating element of the patch antenna on a first side of an electrically insulating substrate of the patch antenna.

The method may comprise defining an electrically conductive back plane of the patch antenna on a second side of the substrate opposite to the first side of the substrate.

The method may comprise coating, printing, painting or otherwise applying an electrically conductive substance to the second side of the substrate so as to form the back plane.

The method may comprise forming the radiating element by coating, printing, painting or otherwise applying an electrically conductive substance to a first side of the substrate.

The method may comprise:

forming the radiating element by coating, printing, painting or otherwise applying an electrically conductive substance to the substrate; and then forming the patch antenna around the core.

The method may comprise forming the radiating element by coating, printing, painting or otherwise applying an electrically conductive substance to the core.

The method may comprise:

forming the radiating element by coating, printing, painting or otherwise applying an electrically conductive substance to the core; and then forming the substrate of the patch antenna on or around the radiating element.

The method may comprise forming the radiating element by coating, printing, painting, wrapping, bonding or otherwise applying an electrically conductive substance to an outer surface of the core.

The method may comprise forming the substrate of the patch antenna on or around the radiating element.

The method may comprise forming the substrate by coating, printing, painting, wrapping, bonding or otherwise applying an electrically insulating substance to the radiating element.

The method may comprise using at least part of the core as an electrically insulating substrate of the patch antenna.

The method may comprise using the confinement member to define the back plane of the patch antenna. For example, the method may comprise using an inner surface of the confinement member to define the back plane of the patch antenna.

It should be understood that one or more of the optional features disclosed in relation to one aspect may apply alone or in any combination in relation to any other aspect.

BRIEF DESCRIPTION OF THE DRAWINGS

The present invention will now be described by way of non-limiting example only with reference to the following figures of which.

DETAILED DESCRIPTION OF THE DRAWINGS

Figure 1:
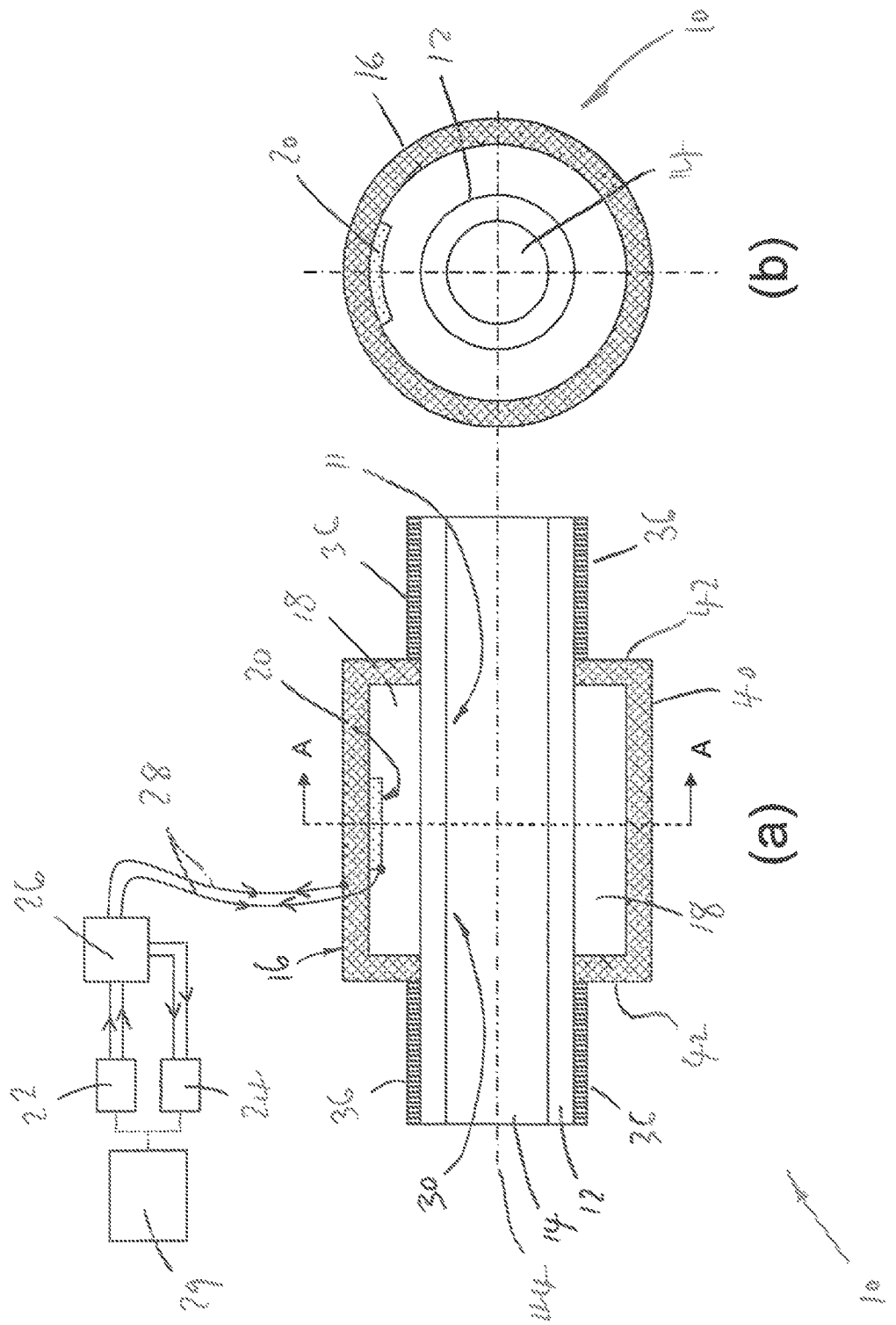
FIG. 1(a) is a schematic longitudinal a cross-section of a first fluid sensor.
FIG. 1(b) is a cross-section on AA of the first fluid sensor of FIG. 1(a)

Referring initially to FIGS. 1(a) and 1(b) there is shown a fluid sensor generally designated 10 which includes an electrically insulating core generally designated 11, a composite confinement member 16 located externally of the core 11 and a patch antenna 20 located between the filler member 18 and the confinement member 16. The core 11 comprises a PEEK base pipe 12 defining a fluid flow path 14 and a PEEK filler member 18 located between the base pipe 12 and the confinement member 16. The confinement member 16 is formed of a composite material which includes carbon fibres embedded in a PEEK matrix.

The fluid sensor 10 comprises an electrical source in the form of an electrical transmitter 22, an electrical detector 24, and a splitter 26 for separating an electrical signal transmitted from the electrical transmitter 22 from an electrical signal received from the patch antenna 20. The splitter 26 is electrically connected to the confinement member 16 and the patch antenna 20 via insulated electrical conductors 28. The fluid sensor 10 further comprises a controller 29. As indicated by the dotted lines in FIG. 1, the controller 29 is configured for communication with the transmitter 22 and the detector 24.

Formed around each end of the base pipe 12 there is provided a composite cuff 36. Each cuff 36 comprises carbon fibres embedded in a PEEK matrix. The carbon fibres in each cuff 36 are wound in a predominantly circumferential direction. The filler member 18 may be formed separately from the base pipe 12 and subsequently located around an axially central section 30 of the base pipe 12 or may be formed directly around the axially central section 30 of the base pipe 12. The confinement member 16 comprises a composite tubular portion 40 and two generally planar composite end portions 42. The carbon fibres in the tubular portion 40 of the confinement member 16 are wound helically over a range of different angles relative to a longitudinal axis 44 of the fluid sensor 10. The confinement member 16 contains the filler member 18, the central section 30 of the base pipe 12 and the fluid flow path 14. The confinement member 16 defines a cavity for an electromagnetic field which extends from the patch antenna 20 through the filler member 18, through the central section 30 of the base pipe 12 and into the fluid flow path 14.

Figure 2:
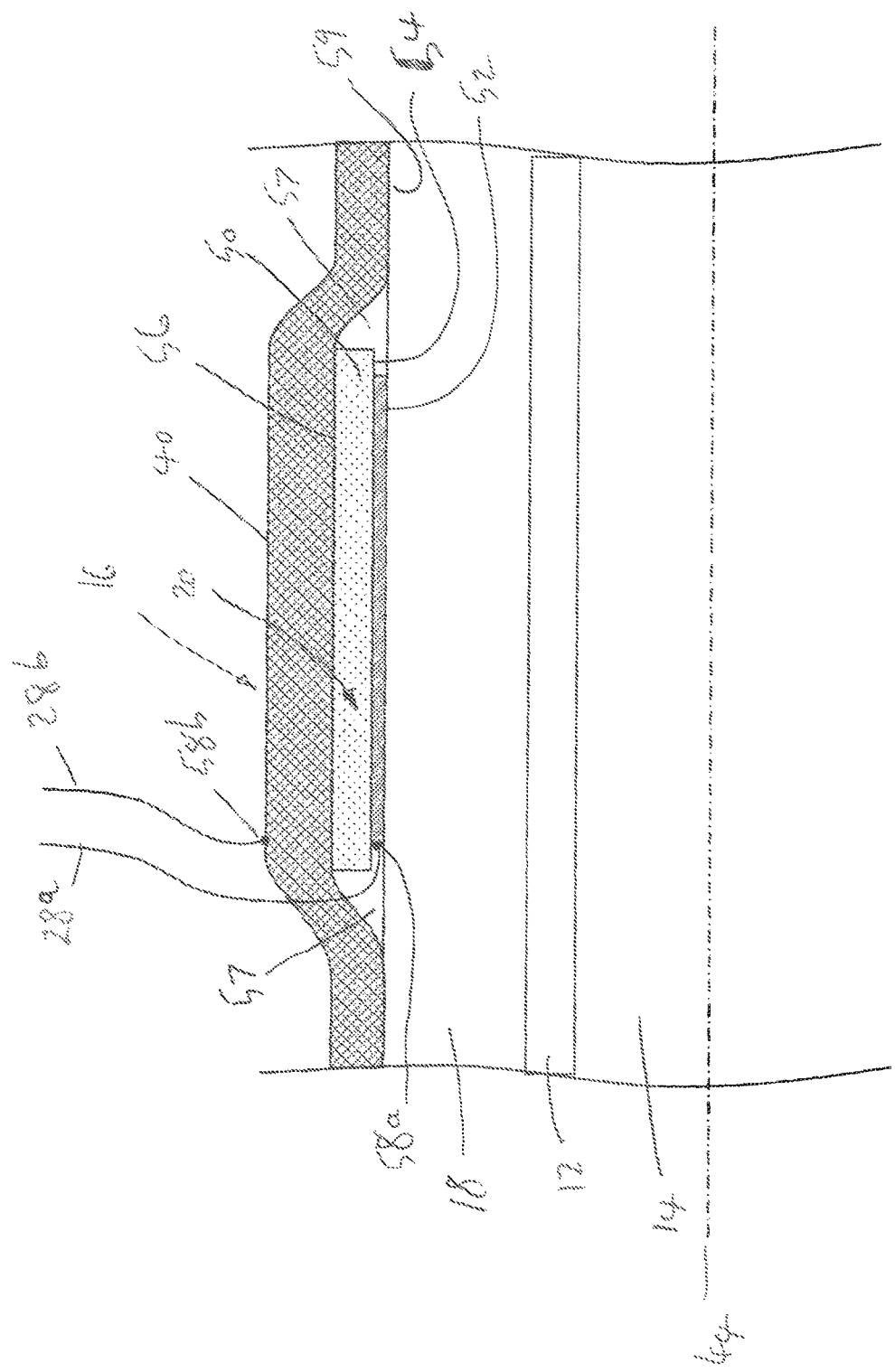
FIG. 2 is a detailed longitudinal cross-section through a wall of the first fluid sensor of FIG. 1(a) in the vicinity of a patch antenna.

FIG. 2 shows a portion of the fluid sensor 10 in the vicinity of the patch antenna 20 in more detail. The patch antenna 20 comprises an electrically insulating substrate 50 and an electrically conductive radiating element 52 located on a radially inner surface 54 of the substrate 50. The tubular portion 40 of the confinement member 16 is formed over a radially outward surface 56 of the substrate 50 of the patch antenna 20 so as to define an electrically conductive backplane. It will be appreciated by one skilled in the art that the relative thicknesses of the radiating element 52 and the substrate 50 of the patch antenna 20 have been exaggerated in FIG. 2 in the interests of clarity and that, in reality, the relative thicknesses of the radiating element 52 and the substrate 50 may be much less than those shown schematically in FIG. 2. As a consequence of the exaggerated thicknesses of the radiating element 52 and the substrate 50, end regions 57 are defined adjacent to the axial ends of the patch antenna 20. One skilled in the art will appreciate that, in reality, the end regions 57 may be much smaller than those shown schematically in FIG. 2.

Moreover, the tubular portion 40 of the confinement member 16 is formed by wrapping a tape, strip or the like of carbon fibres embedded in a PEEK matrix around the radially outward surface 56 of the substrate 50 and subjecting the tape, strip or the like to high temperatures which are sufficient to soften or melt the PEEK matrix sufficiently to cause the PEEK matrix to comply with or flow into the end regions 57 such that the end regions 57 become substantially or completely filled with PEEK to thereby eliminate any air gaps for improved mechanical strength and, in particular, for improved pressure integrity of the fluid sensor 10.

One electrical conductor 28*a* is soldered or otherwise electrically connected to the radiating element 52 so as to form an electrical connection 58*a* therewith. The other electrical conductor 28*b* is soldered or otherwise electrically connected to the confinement member 16 so as to form an electrical connection 58*b* therewith.

Figure 3:
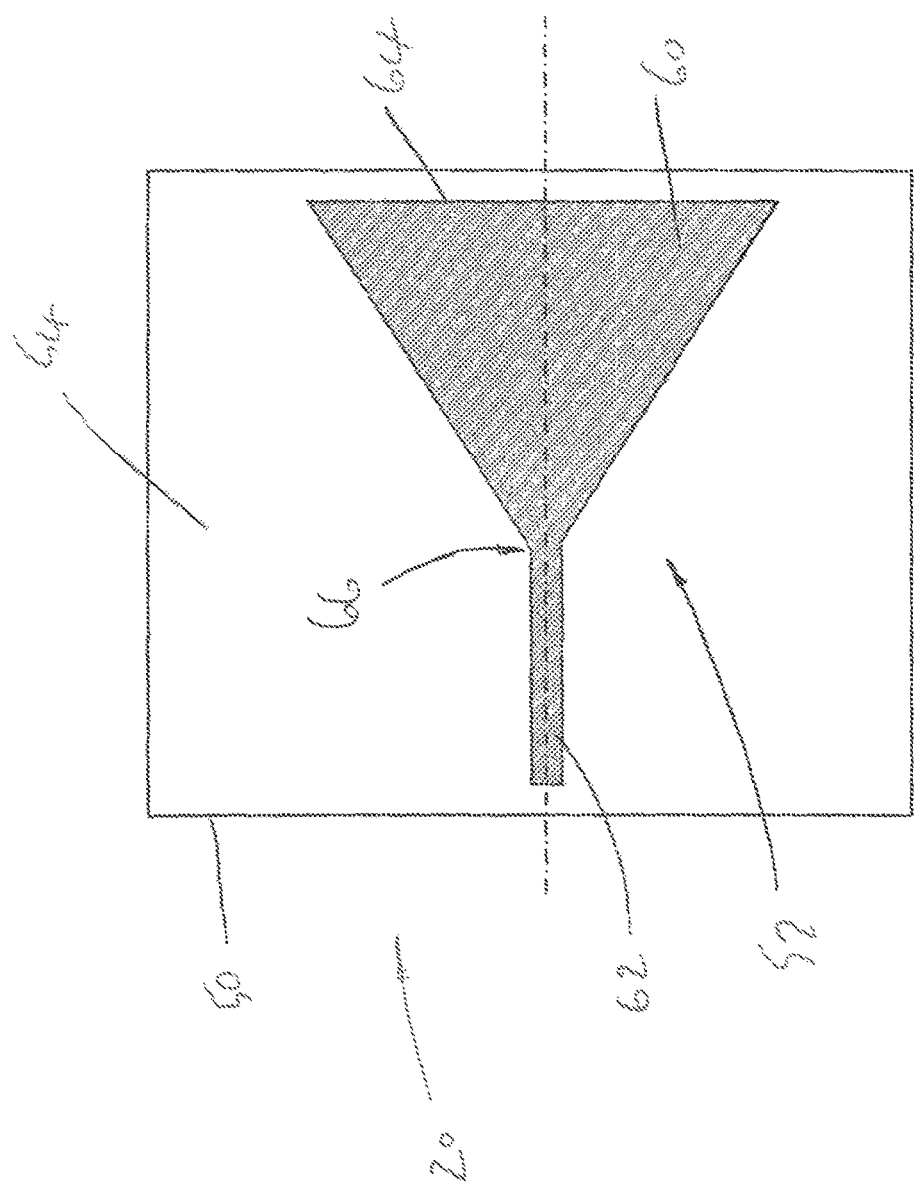
FIG. 3 is a view of an inner side of the patch antenna of the first fluid sensor of FIG. 1(a) showing a radiating element of the patch antenna before incorporation of the patch antenna into the first fluid sensor.

FIG. 3 shows the patch antenna 20 in isolation before incorporation into the fluid sensor 10. The substrate 50 is generally flexible. Prior to incorporation into the fluid sensor 10, the substrate 50 is generally planar. This permits the radiating element 52 to be defined on the substrate 50 and the patch antenna 20 to be fitted around an outer surface 59 of the filler member 80. The radiating element 52 is formed by printing or otherwise applying an electrically conductive substance comprising carbon onto selective areas of the substrate 50 so as to define a generally triangular main body portion 60 of the radiating element 52 and a waveguide portion 62 of the radiating element 52. The triangular main body portion 60 of the radiating element 52 has a base edge 64 and an apex 66 opposite the base edge. The waveguide portion 62 of the radiating element 52 joins the main body portion 60 of the radiating element 52 at the apex 66.

In use, the transmitter 22 applies a swept frequency RF electrical signal between the confinement member 16 and the patch antenna 20 via the splitter 26 and the electrical conductors 28*a* and 28*b*. The patch antenna 20 couples the applied RF electrical signal to an RF electromagnetic field confined within the cavity defined by the confinement member 16. Both the PEEK filler member 18 and the PEEK central section 30 of the base pipe 12 are substantially transparent to electromagnetic radiation at the frequency of the applied RF electrical signal. The RF electromagnetic field extends from the patch antenna 20 through the filler member 18, the central section 30 of the base pipe 12 and at least a portion of the fluid flow path 14 to the confinement member 16.

The predominantly circumferential orientation of the carbon fibres in the composite cuffs 36 improves containment of electromagnetic energy within the cavity by suppressing the transmission of one or more electromagnetic modes from the cavity along the base pipe 12 and along any pipe coupled to the axial ends of the base pipe 12 as described in more detail in the Applicant's co-pending UK patent application no. 1302969.9.

The patch antenna 20 couples the RF electromagnetic field back to generate a return RF electrical signal which travels back along the electrical conductors 28*a* and 28*b* to the detector 24 via the splitter 26. The detected RF electrical signal as a function of the frequency of the transmitted electrical signal defines a frequency response of the fluid sensor 10 which depends upon the contents of the fluid flow path 14. In particular, the frequency response of the fluid sensor 10 depends upon the composition and/or flow rate of any fluid present in the fluid flow path 14. The controller 29 is configured to determine the composition and/or flow rate of any fluid in the fluid flow path 14 from one or more features in the frequency response of the fluid sensor 10. For example, the controller 29 is configured to determine the composition and/or flow rate of any fluid in the fluid flow path 14 from the resonant frequency, size and/or shape of one or more resonant features such as one or more resonant peaks and/or dips observed in the frequency response of the fluid sensor 10.

Figure 4:
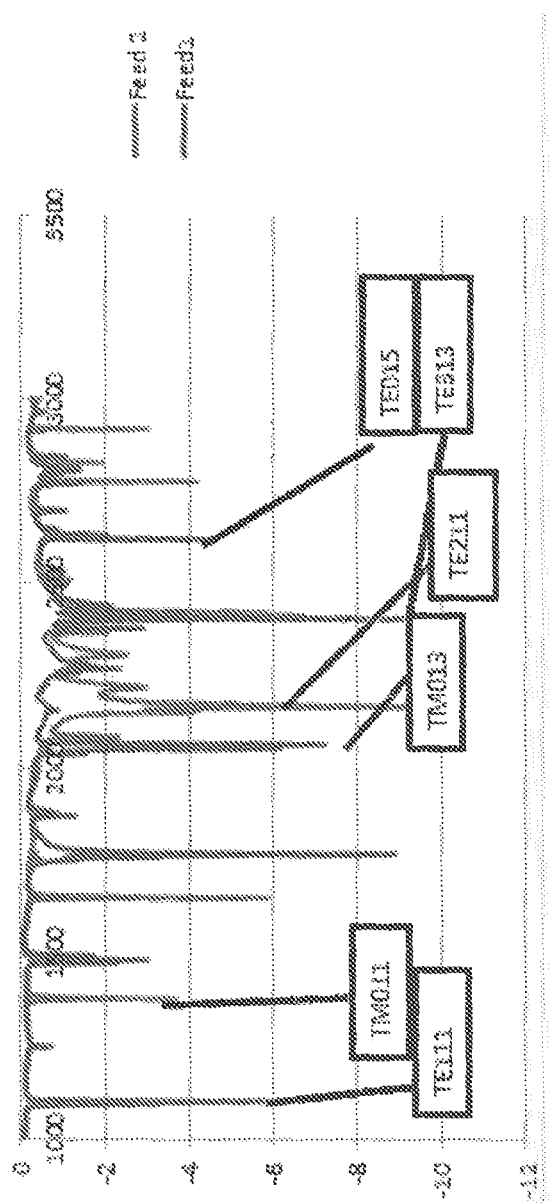
FIG. 4 is a simulated frequency response spectrum for the first fluid sensor of FIG. 1(a) for different orientations of the patch antenna.

FIG. 4 shows simulated frequency responses of the fluid sensor 10 for two different orientations of the radiating element 52. The simulated frequency responses of FIG. 4 were generated for a radiating element 52 for which the base edge 64 is 39 mm long and for which the distance from the base edge 64 to the apex 66 is 48 mm. The fluid flow path 14 was assumed to be full of air. The frequency response labelled "Feed 1" corresponds to an orientation of the base edge 64 of the radiating element 52 aligned parallel to the longitudinal axis 44 of the fluid sensor 10. The frequency response labelled "Feed 2" corresponds to an orientation of the base edge 64 of the radiating element 52 aligned circumferentially with respect to the longitudinal axis 44 of the fluid sensor 10. Thus, FIG. 4 demonstrates that the orientation of the radiating element 52 may be selected so as to provide the fluid sensor 10 with a predetermined frequency response for a predetermined set of contents of the fluid flow path 14. Additionally or alternatively, the geometry of the radiating element 52 may be selected so as to provide the fluid sensor 10 with a predetermined frequency response for a predetermined range of fluid compositions and/or fluid flow rates in the fluid flow path 14. For example, the dimensions of the sides of the triangular main body portion 60 and the angles therebetween may be varied so as to provide the fluid sensor 10 with a predetermined frequency response for a predetermined range of fluid compositions and/or fluid flow rates in the fluid flow path 14.

Figure 5:
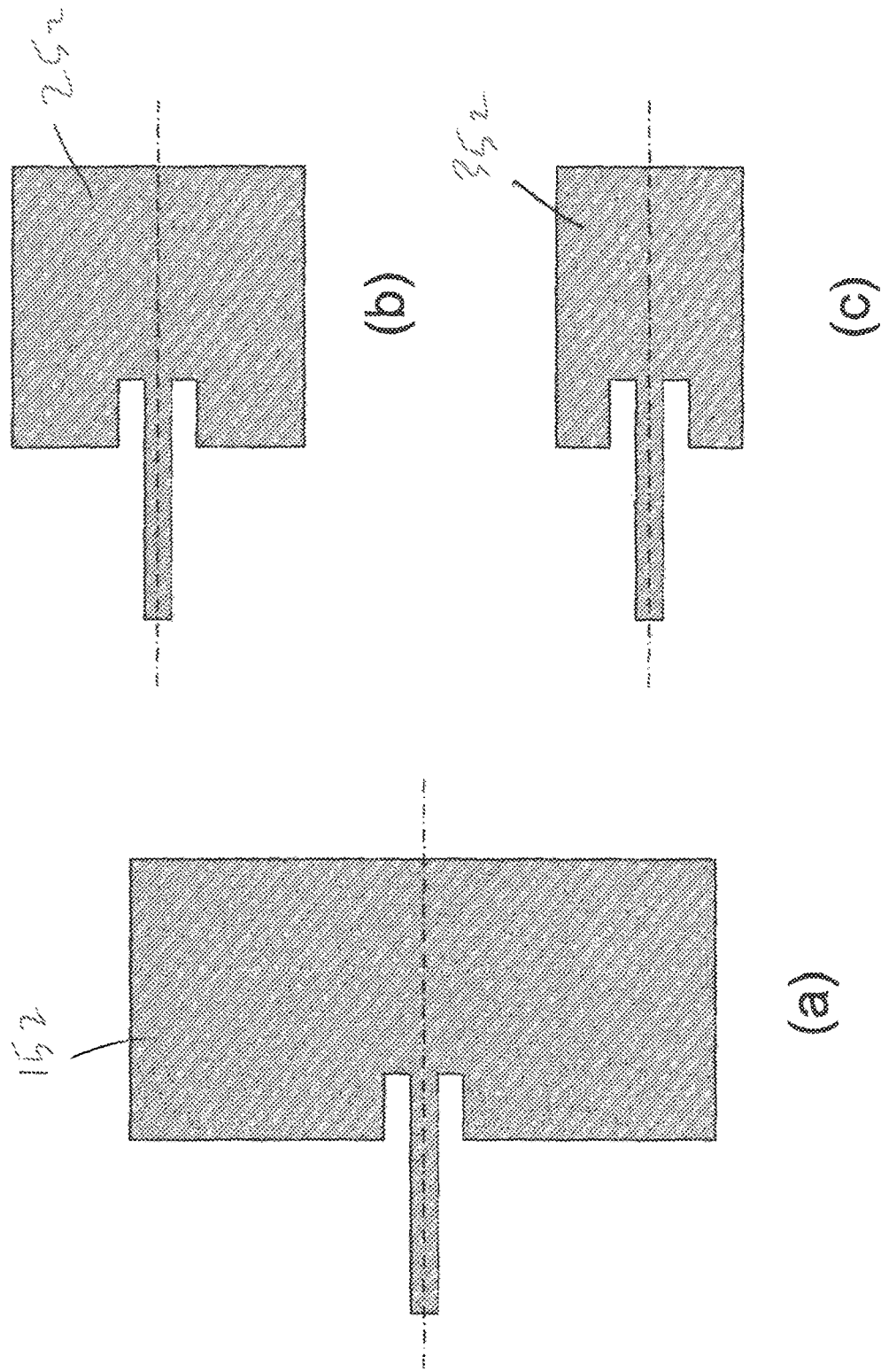
FIG. 5(a) is a view of a first alternative radiating element for the patch antenna of the first fluid sensor of FIG. 1(a)
FIG. 5(b) is a view of a second alternative radiating element for the patch antenna of the first fluid sensor of FIG. 1(a)
FIG. 5(c) is a view of a third alternative radiating element for the patch antenna of the first fluid sensor of FIG. 1(a)
Figure 6:
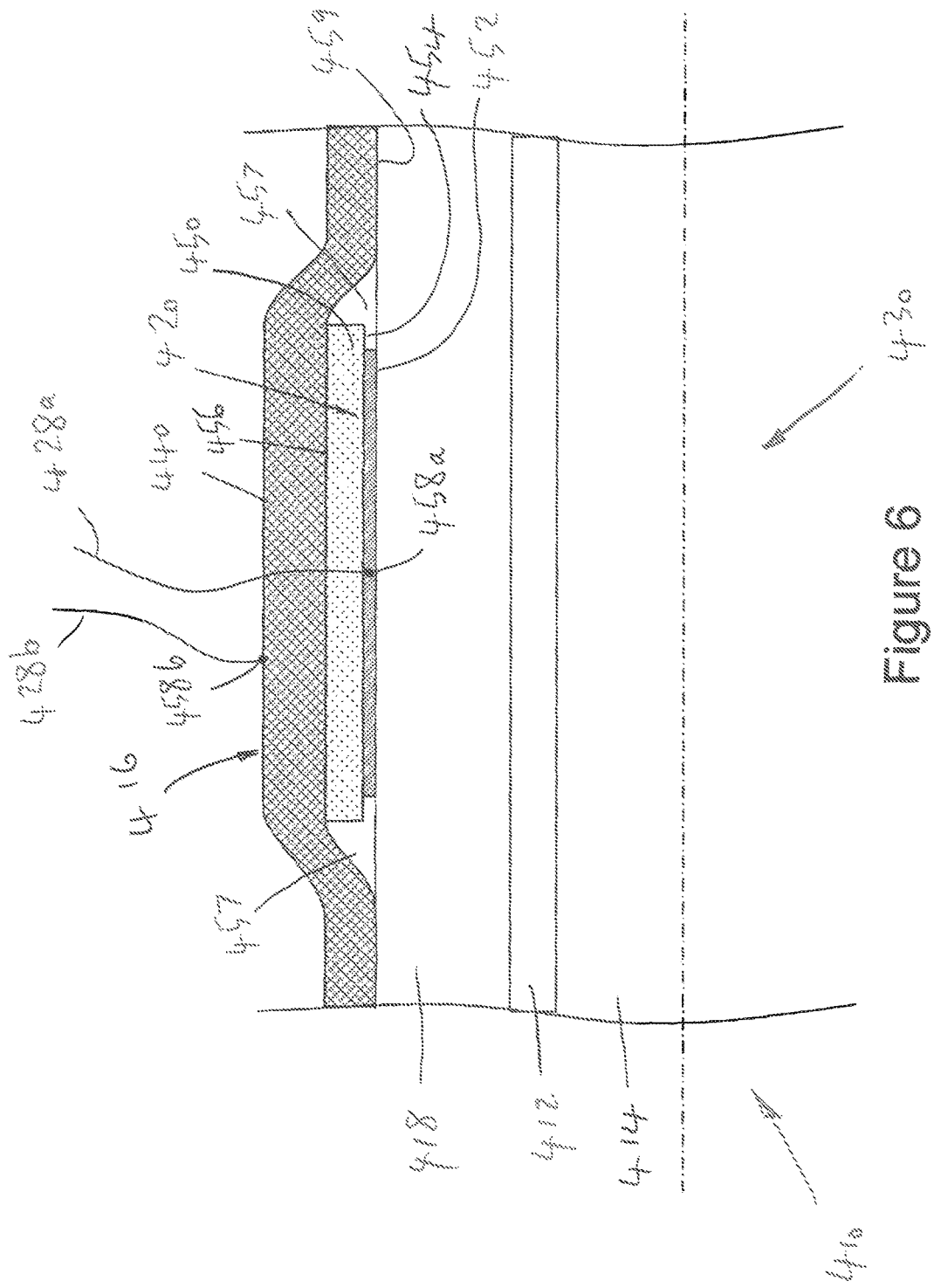
FIG. 6 is a detailed longitudinal cross-section through a wall of a second fluid sensor in the vicinity of a patch antenna.

Examples of alternative radiating elements 152, 252 and 352 for use with the fluid sensor 10 are shown in FIGS. 5(*a*)-5(*c*) respectfully. Each radiating element 152, 252 and 352 has a generally rectangular geometry but a different aspect ratio. One of the radiating elements 152, 252 and 352 may be employed to provide the fluid sensor 10 with a predetermined frequency response for a predetermined range of fluid compositions and/or fluid flow rates in the fluid flow path 14. Referring to FIG. 6 there is shown an axially central section 430 of a second fluid sensor 410 in the vicinity of a patch antenna 420. Like the fluid sensor 10 described with reference to FIGS. 1 to 3, the second fluid sensor 410 shown in FIG. 6 comprises a PEEK core 411 which includes a PEEK base pipe 412 and a PEEK filler member 418. The PEEK base pipe 412 defines a fluid flow path 414. A composite confinement member 416 is located externally of the PEEK core 411. The composite confinement member 416 comprises carbon fibres embedded in a PEEK matrix.

The patch antenna 420 comprises an electrically insulating substrate 450 and an electrically conductive radiating element 452 located on a radially inner surface 454 of the substrate 450. A tubular portion 440 of the confinement member 416 is formed over a radially outward surface 456 of the substrate 450 of the patch antenna 420 so as to define an electrically conductive backplane. Like the PEEK-filled end regions 57 defined adjacent to the axial ends of the patch antenna 20 shown in FIG. 2, PEEK-filled end regions 457 are defined adjacent to the axial ends of the patch antenna 420. In contrast to the electrical conductor 28a of the fluid sensor 10 shown in FIG. 2, the second fluid sensor 410 comprises an electrical conductor 428a which extends through the substrate 450 of the patch antenna 420 and which is soldered or otherwise electrically connected to the radiating element 452 so as to form an electrical connection 458a therewith, which electrical connection 458a is located substantially at the centre of the radiating element 452. Like the other electrical conductor 28b of the fluid sensor 10 shown in FIG. 2, the other electrical conductor 428b of the fluid sensor 410 shown in FIG. 6 is soldered or otherwise electrically connected to the confinement member 416 so as to form an electrical connection 458b therewith.

Figure 7:
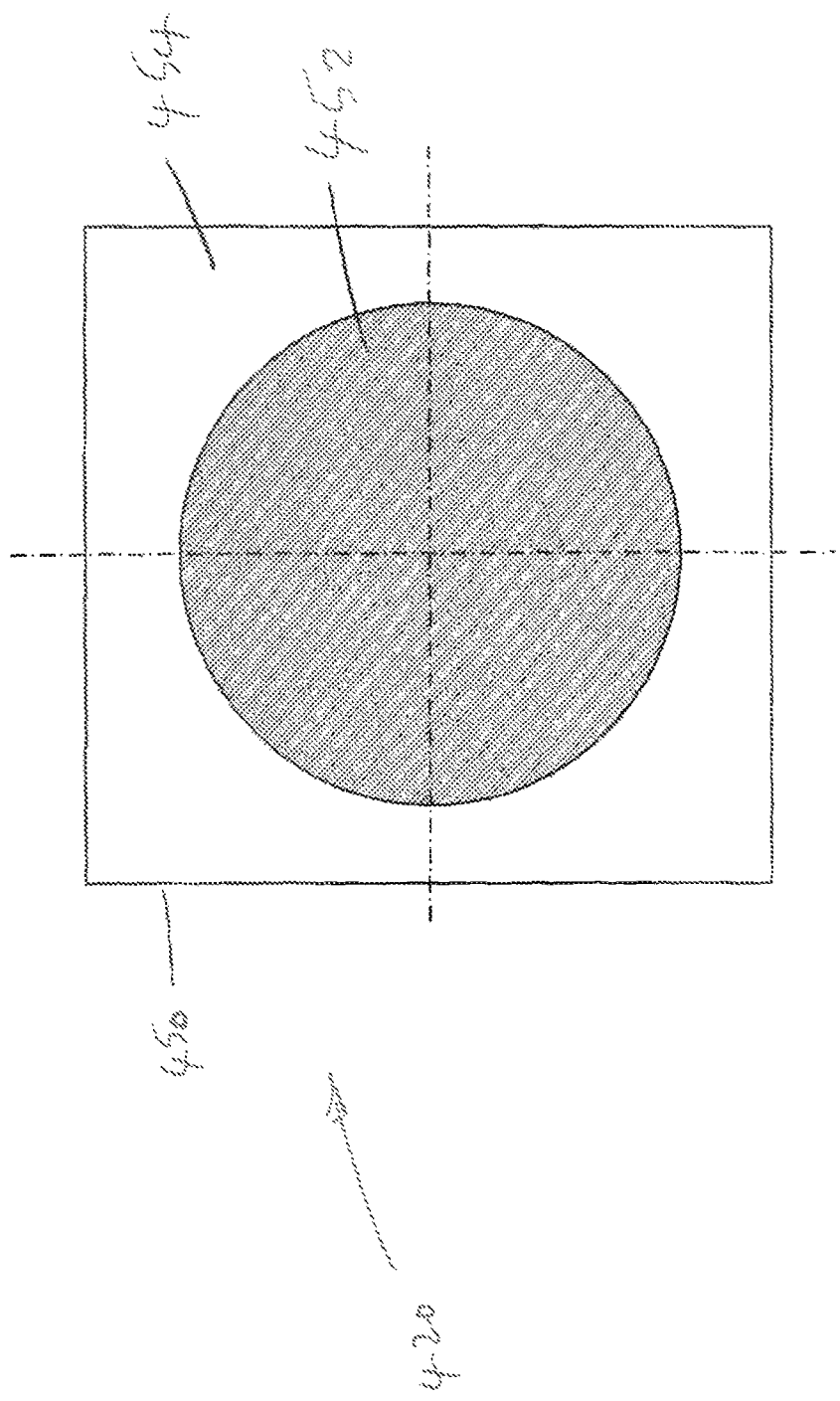
FIG. 7 is a view of an inner side of the patch antenna of the second fluid sensor of FIG. 6 showing a radiating element of the patch antenna before incorporation of the patch antenna into the second fluid sensor.

The patch antenna 420 of the fluid sensor 410 is shown in more detail in FIG. 7. The radiating element 452 is circular. The radius of the radiating element 452 may be selected to provide the fluid sensor 410 with a predetermined frequency response for a predetermined range of fluid compositions and/or fluid flow rates in the fluid flow path 414.

Figure 8:
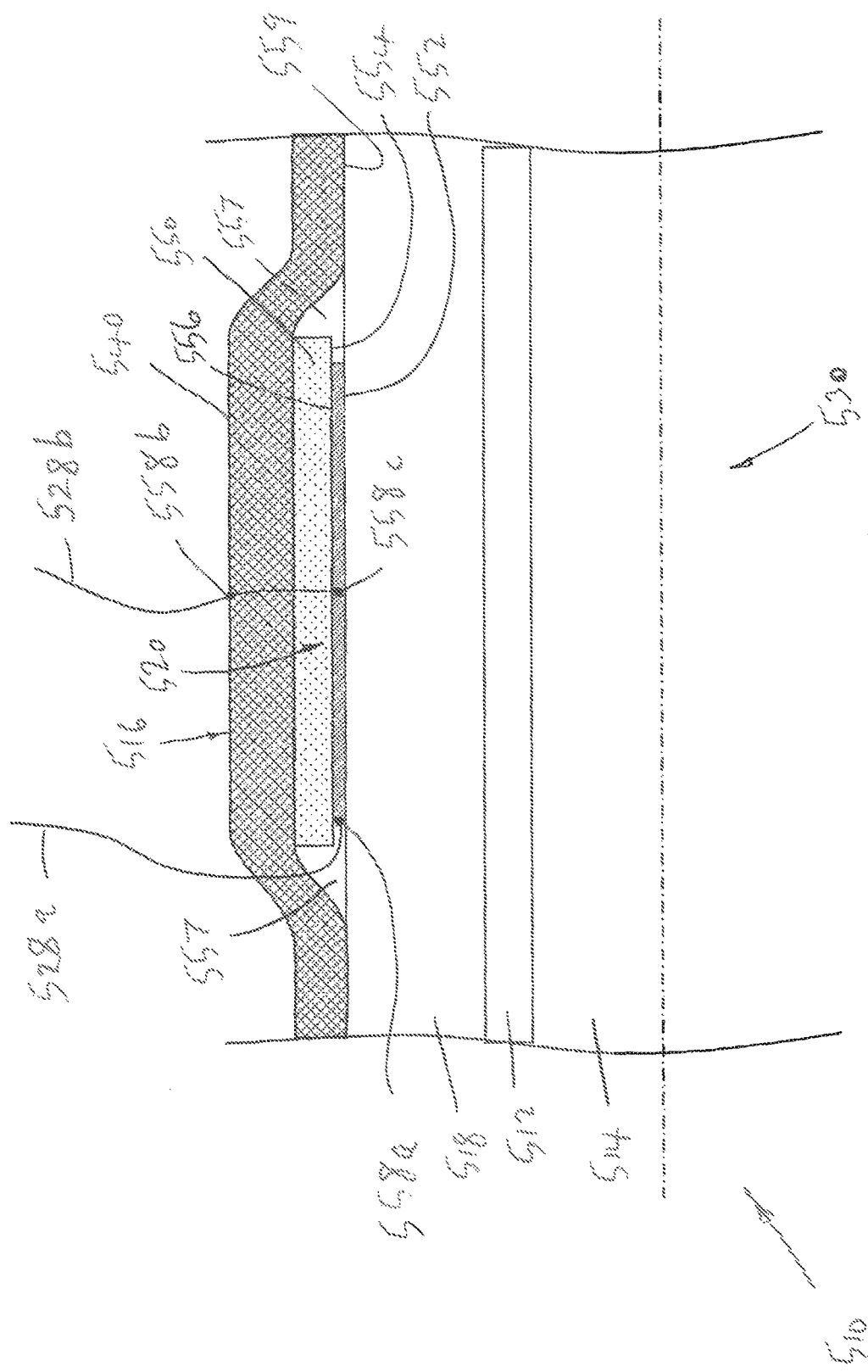
FIG. 8 is a detailed longitudinal cross-section through a wall of a third fluid sensor in the vicinity of a patch antenna.

Referring to FIG. 8 there is shown an axially central section 530 of a third fluid sensor 510 in the vicinity of a patch antenna 520. Like the fluid sensor 10 described with reference to FIGS. 1 to 3, the third fluid sensor 510 shown in FIG. 8 comprises a PEEK core 511 which includes a PEEK base pipe 512 and a PEEK filler member 518. The PEEK base pipe 512 defines a fluid flow path 514. A composite confinement member 516 is located externally of the PEEK core 511. The composite confinement member 516 comprises carbon fibres embedded in a PEEK matrix.

The patch antenna 520 comprises an electrically insulating substrate 550 and an electrically conductive radiating element 552 located on a radially inner surface 554 of the substrate 550. A tubular portion 540 of the confinement member 516 is formed over a radially outward surface 556 of the substrate 550 of the patch antenna 520 so as to define an electrically conductive backplane. Like the PEEK-filled end regions 57 defined adjacent to the axial ends of the patch antenna 20 shown in FIG. 2, PEEK-filled end regions 557 are defined adjacent to the axial ends of the patch antenna 520. Like the electrical conductor 22a of the fluid sensor 10 shown in FIG. 2, the third fluid sensor 510 comprises an electrical conductor 528a which extends through the confinement member 516 and which is soldered or otherwise electrically connected to the radiating element 552 so as to form a first electrical connection 558a with the radiating element 552. Like the other electrical conductor 28b of the fluid sensor 10 shown in FIG. 2, the other electrical conductor 528b of the fluid sensor 510 shown in FIG. 8 is soldered or otherwise electrically connected to the confinement member 516 so as to form an electrical connection 558b therewith. In contrast to the fluid sensor 10 shown in FIG. 2, however, the other electrical conductor 528b of the fluid sensor 510 shown in FIG. 8 is also soldered or otherwise electrically connected to the radiating element 552 so as to form a second electrical connection 558c with the radiating element 552.

Figure 9:
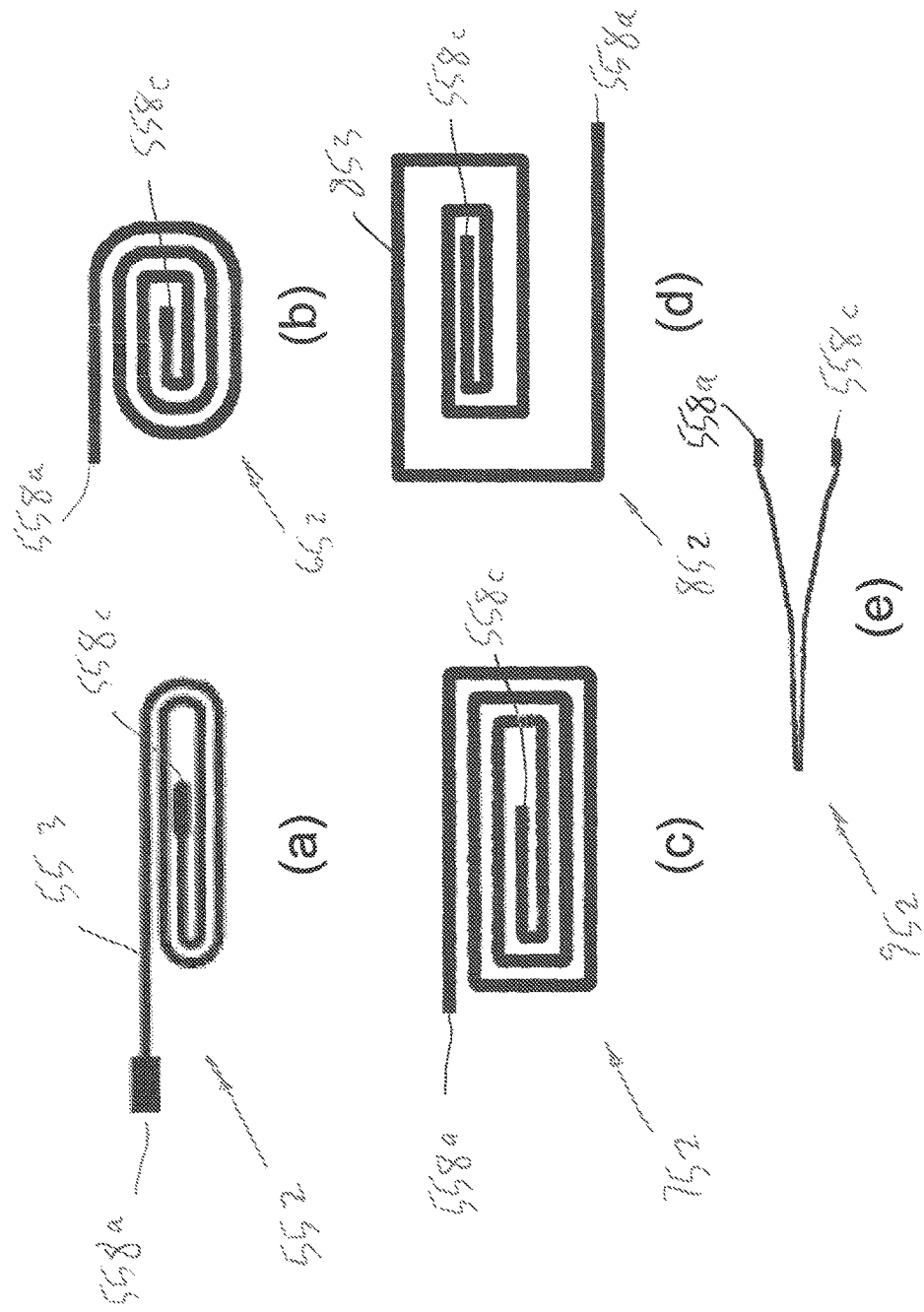
FIG. 9(a) is a view of a radiating element of the patch antenna of the third fluid sensor of FIG. 8.
FIG. 9(b) is a view of a first alternative radiating element for the patch antenna of the third fluid sensor of FIG. 8.
FIG. 9(c) is a view of a second alternative radiating element for the patch antenna of the third fluid sensor of FIG. 8.
FIG. 9(d) is a view of a third alternative radiating element for the patch antenna of the third fluid sensor of FIG. 8.
FIG. 9(e) is a view of a fourth alternative radiating element for the patch antenna of the third fluid sensor of FIG. 8.

The radiating element 552 of the patch antenna 520 of the fluid sensor 510 is shown in more detail in FIG. 9(*a*). The radiating element 552 defines a generally spiral or convoluted electrically conductive path 553. The first and second electrical connections 558a, 558c are located at opposite ends of the path 553. Such a radiating element 552 may be designed so as to have a predetermined inductance for improved impedance matching and, therefore, improved coupling efficiency between the radiating element 552 and the electromagnetic field created in the cavity defined by the confinement member 516.

FIGS. 9(*b*)-9(*e*) show alternative radiating elements 652, 752, 852 and 952 for use with the patch antenna 520 of the fluid sensor 510. Each radiating element 652, 752, 852, 952 may be configured to provide the fluid sensor 510 with a predetermined frequency response for a predetermined range of fluid compositions and/or fluid flow rates in the fluid flow path 514. The radiating element 852 of FIG. 9(*d*) defines a generally spiral or convoluted electrically conductive path 853. The first and second electrical connections 558a, 558c are located at opposite ends of the path 853. The coil or curvature of the radiating element 852 decreases towards the centre of the radiating element 852 i.e. the spacing between adjacent windings reduces towards the centre of the radiating element 852. This has the effect of reducing the effective inductor length at higher frequencies because the closer turns, short out and, combined with the lower effective capacitance at higher frequency, means that the patch antenna 520 including the radiating element 852 has a relatively constant impedance across a broadband transmission range. This may provide broadband impedance matching and improved coupling efficiency between the radiating element 852 and the electromagnetic field created in the cavity defined by the confinement member 516.

Figure 10:
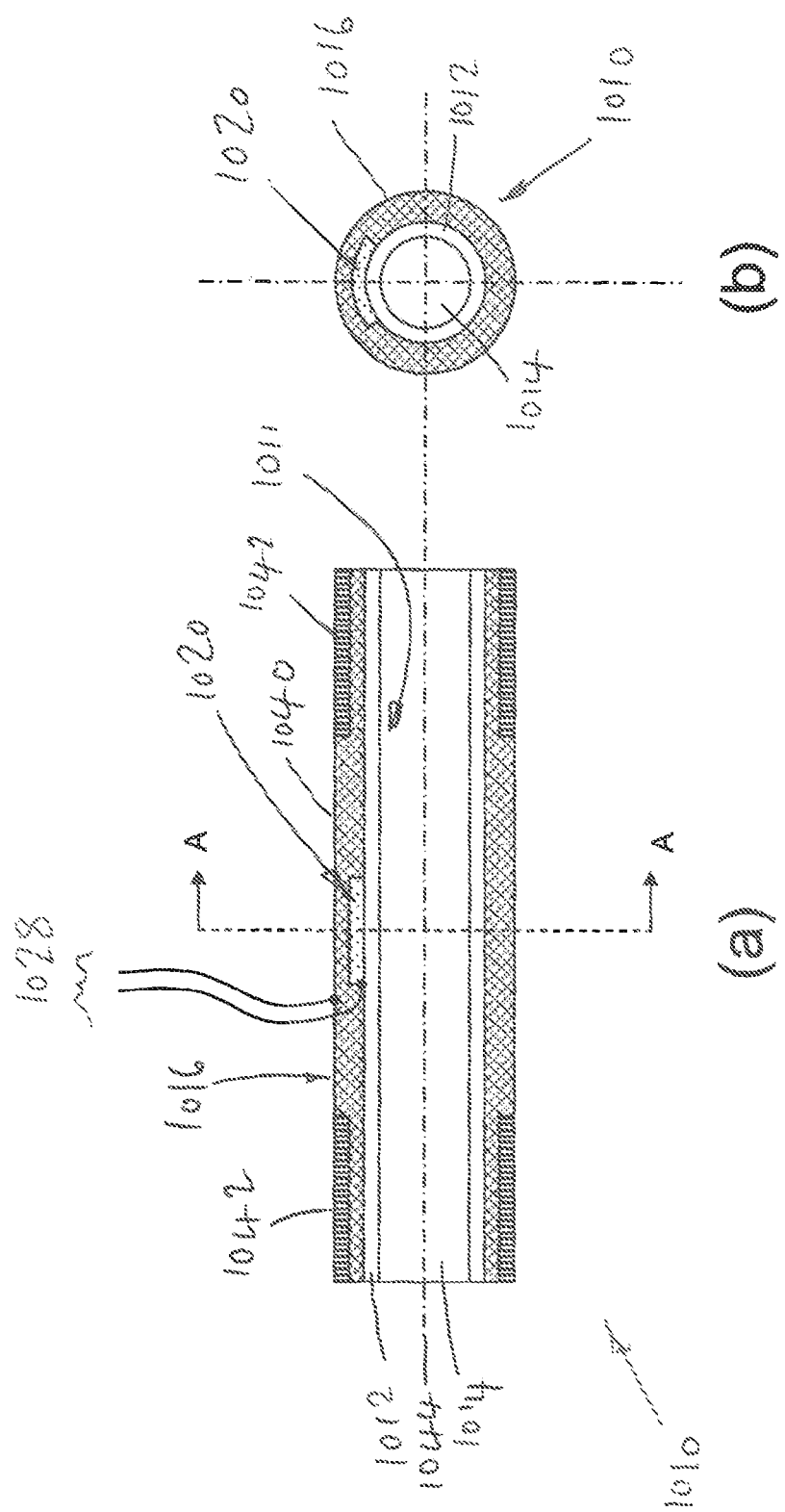
FIG. 10(a) is a schematic longitudinal cross-section of a fourth fluid sensor.
FIG. 10(b) is a cross-section on AA of the fourth fluid sensor of FIG. 10(a)

Referring to FIGS. 10(*a*) and 10(*b*) there is shown a fourth fluid sensor generally designated 1010 comprising an electrically insulating core generally designated 1011 and a composite confinement member 1016 located externally of the core 1011. The core 1011 comprises a PEEK base pipe 1012 defining a fluid flow path 1014. Unlike the fluid sensor 10 of FIGS. 1(*a*) and 1(*b*), the fluid sensor 1010 of FIGS. 10(*a*) and 10(*b*) does not have a filler member of any kind located between the base pipe 1012 and the confinement member 1016. The confinement member 1016 is formed of a composite material which includes carbon fibres embedded in a PEEK matrix.

The fluid sensor 1010 further comprises a patch antenna 1020 located between the base pipe 1012 and the confinement member 1016. Insulated electrical conductors 1028 provide external electrical connections to the confinement member 1016 and the patch antenna 1020 for applying RE electrical signals to the fluid sensor 1010 and receiving RF electrical signals from the fluid sensor 1010.

The confinement member 1016 comprises a composite tubular axially central section 1040 and two tubular cuffs 1042 located at opposite axial ends of the axially central section 1040. The carbon fibres in the central section 1040 of the confinement member 1016 are wound helically over a range of different angles relative to a longitudinal axis 1044 of the fluid sensor 1010. The carbon fibres in each cuff 1042 are wound in a predominantly circumferential direction. The suppression of the electromagnetic cavity modes provided by the cuffs 1042 is sufficient to avoid any requirement for a filler member between the base pipe 1012 and the confinement member 1016.

In the absence of a filler member, the fluid sensor 1010 of FIGS. 10(a) and 10(b) may be simpler and, therefore, less expensive to manufacture than the fluid sensor 10 of FIGS. 1(a) and 1(b). Moreover, the fluid sensor 1010 of FIGS. 10(a) and 10(b) may have improved structural strength and environmental integrity relative to the fluid sensor 10 of FIGS. 1(a) and 1(b). For example, the fluid sensor 1010 of FIGS. 10(a) and 10(b) may be able to withstand higher internal fluid pressures within the fluid flow path 1014 and/or higher external fluid pressures which act on an outer surface of the confinement member 1016 compared with the fluid sensor 10 of FIGS. 1(a) and 1(b). Unlike the fluid sensor 10 of FIGS. 1(a) and 1(b), the fluid sensor 1010 of FIGS. 10(a) and 10(b) has a uniform outer diameter, This may simplify deployment of the fluid sensor 1010 compared with the deployment of the fluid sensor 10 of FIGS. 1(a) and 1(b), especially where the outer diameter of the fluid sensor 1010 is substantially matched to an outer diameter of a tubing string such as a marine riser into which the fluid sensor 1010 is incorporated.

It should be understood that any of the radiating elements described with reference to FIGS. 2, 3, 5(a)-5(c), 6, 7, 8 and 9(a)-9(e) may be used with the fluid sensor 1010 of FIGS. 10(a) and 10(b).

Figure 11:
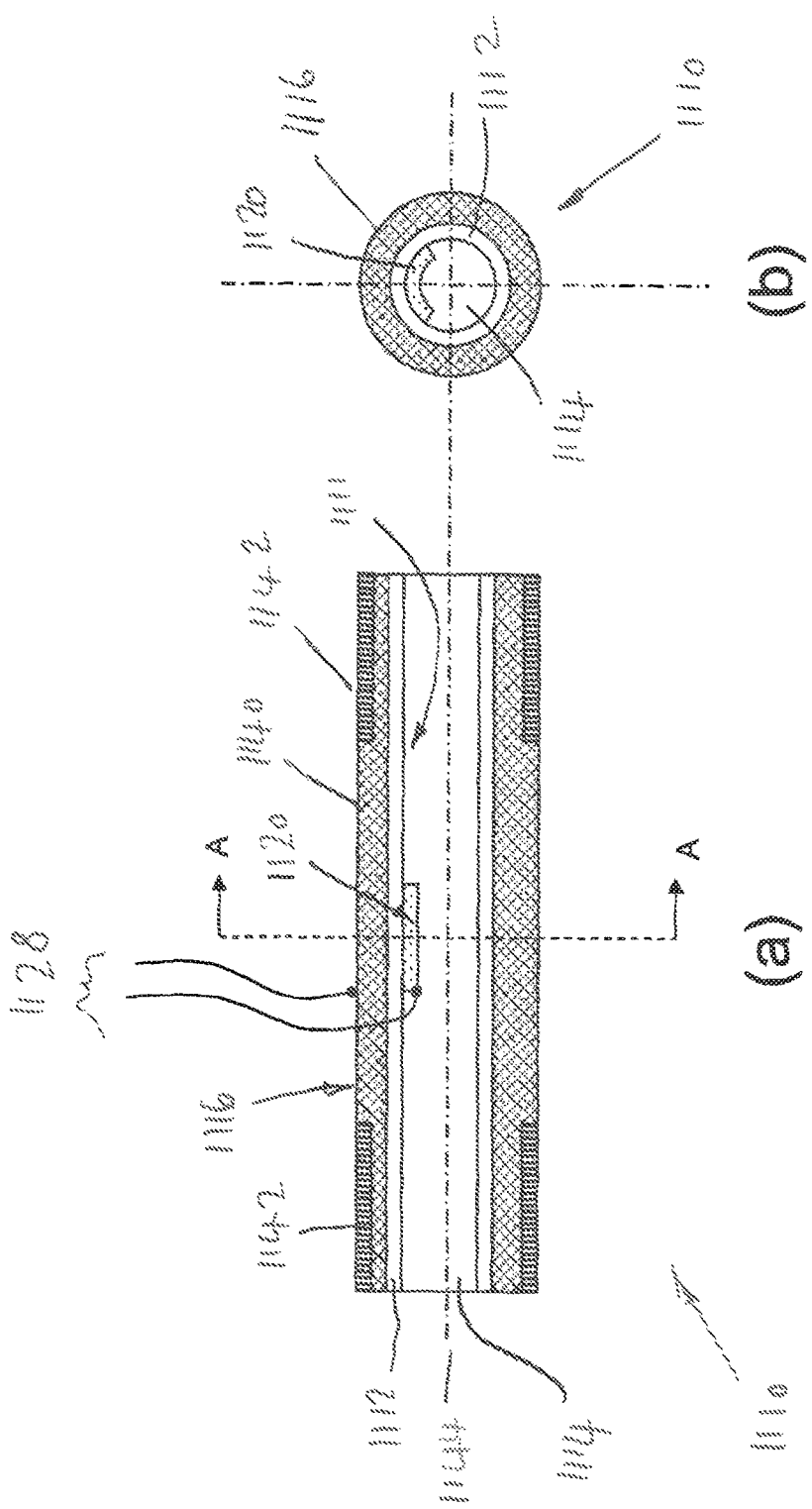
FIG. 11(a) is a schematic longitudinal cross-section of a fifth fluid sensor.
FIG. 11(b) is a cross-section on AA of the fifth fluid sensor of FIG. 11(a).

A fifth fluid sensor generally designated 1110 is shown in FIGS. 11(a) and 11(b). The fifth fluid sensor 1110 comprises many like features with the fourth fluid sensor 1010 of FIGS. 10(a) and 10(b) and, as such, like features share like reference numerals. The fifth fluid sensor 1110 comprises an electrically insulating core generally designated 1111 and a composite confinement member 1116 located externally of the core 1111. The core 1111 comprises a PEEK base pipe 1112 defining a fluid flow path 1114. The confinement member 1116 is formed of a composite material which includes carbon fibres embedded in a PEEK matrix.

The fluid sensor 1110 further comprises a patch antenna 1120. Unlike the patch antenna 1020 of the fourth fluid sensor 1010 of FIGS. 10(a) and 10(b), however, the patch antenna 1120 of the fluid sensor 1110 of FIGS. 11(a) and 11(b) is located on an inner surface of the base pipe 1112 within the fluid flow path 1114. The patch antenna 1120 extends into the fluid flow path 1114. This may improve the efficiency of coupling between the electromagnetic field and any fluid present in the fluid flow path 1114. The profile of the patch antenna may be sufficiently low to minimise any obstruction to the flow of fluid along the fluid flow path 1114 and to minimise the build up of hydrates, wax, particulates, or other solid matter on the patch antenna. Similarly, the profile of the patch antenna may be sufficiently low to permit the passage of objects along the fluid flow path 1114, for example for the purposes of mechanical cleaning or pigging of the fluid flow path 1114.

Insulated electrical conductors 1128 provide external electrical connections to the confinement member 1116 and the patch antenna 1120 for applying an RF electrical signal to the fluid sensor 1110 and for receiving an RF electrical signal from the fluid sensor 1110.

The confinement member 1116 comprises a composite tubular axially central section 1140 and two tubular cuffs 1142 located at opposite axial ends of the axially central section 1140. The carbon fibres in the central section 1140 of the confinement member 1116 are wound helically over a range of different angles relative to a longitudinal axis 1144 of the fluid sensor 1110. The carbon fibres in each cuff 1142 are wound in a predominantly circumferential direction. The suppression of the electromagnetic cavity modes provided by the cuffs 1142 is sufficient to avoid any requirement for a filler member between the base pipe 1112 and the confinement member 1116.

It should be understood that any of the radiating elements described with reference to FIGS. 2, 3, 5(a)-5(c), 6, 7, 8 and 9(a)-9(e) may be used with the fluid sensor 1110 of FIGS. 11(a) and 11(b).

One skilled in the art will appreciate that the fluid sensors described above may be modified without departing from the scope of the present invention as defined by the claims. For example, rather than being formed from PEEK, an axially central section of the base pipe which is located between the patch antenna and the fluid flow path such as the axially central section 30 of the base pipe 12 may be formed from any material which transmits or is substantially transparent to electromagnetic radiation at the frequency of the applied RF electrical signals. The axially central section 30 of the base pipe 12 may, for example, comprise one or more glass fibre reinforcing elements embedded in a matrix material such as PEEK.

The confinement member may comprise a metal such as copper.

The radiating element of the patch antenna may be applied directly to the outer surface of the filler member or to the outer surface of the base pipe. For example, the radiating element may be printed or painted directly to the outer surface of the filler member or to the outer surface of the base pipe. The substrate of the patch antenna may then be formed in situ on or around such a radiating element.

The patch antenna may be configured to couple energy from the electrical signal source to the electromagnetic field.

The patch antenna may be configured to couple energy from the electromagnetic field to the electrical detector.

The fluid sensors described above each have a folded fluid sensor geometry in which the patch antenna serves as both a transmitting and receiving antenna. However, in other fluid sensors, different antennas may be used for transmitting and receiving. Such an unfolded fluid sensor geometry may avoid any requirement for an electrical signal separation device such as the splitter 26 shown in FIG. 1.

The fluid sensor may comprise a further antenna.

The further antenna may comprise a further patch antenna.

The further antenna may comprise an antenna of a kind other than a patch antenna. For example, the further antenna may comprise at least one of a monopole antenna and a loop antenna or the like.

One of the patch antenna and the further antenna may be configured to couple energy from the electrical signal source to the electromagnetic field and the other of the patch antenna and the further antenna may be configured to couple energy from the electromagnetic field to the electrical detector.

Such an unfolded fluid sensor geometry may avoid any requirement for an electrical signal separation device.

The cavity defined by the confinement member 16 of FIG. 1 is a resonant cavity for one or more electromagnetic modes. The properties of the one or more electromagnetic modes such as the resonant frequencies of the one or more electromagnetic modes depend on the configuration of the cavity and/or on the contents of the cavity including any fluid present in and/or flowing through the fluid flow path. Such a resonant cavity may provide enhanced measurement sensitivity of a composition and/or flow rate of any fluid present in and/or flowing through the fluid flow path.

The cavity may be a non-resonant cavity. The cavity may be configured so as to at least partially suppress any resonant features existing on the electrical signal detected by the electrical detector. The cavity may be configured so as to at least partially suppress interference effects between a electromagnetic wave transmitted into the cavity and an electromagnetic wave reflected within the cavity. The cavity may be configured so as to at least partially suppress the formation of any significant standing waves within the cavity.

The electrical source may comprise a gain element.

The gain element and the cavity defined by the confinement member may together define an oscillator capable of generating one or more resonant oscillator modes. Each oscillator mode may be associated with one or more corresponding resonant features of a frequency spectrum of an electrical signal detected by the electrical detector. In such an arrangement, the frequencies of the resonant oscillator modes may be more sensitive to a composition and/or flow rate of any fluid present in and/or flowing through the fluid flow path than an arrangement in which the cavity defined by the confinement member lies outside or does not form part of a cavity of the oscillator.

The controller may be configured to determine the contents of the cavity defined by the confinement member including any fluid present in and/or flowing through the fluid flow path from the one or more resonant features in a frequency spectrum of the detected signal.

The one or more resonant features of the detected signal may comprise one or more resonant peaks and/or one or more resonant dips in the frequency spectrum of the detected signal.

The gain element may comprise at least one of an amplifier, a gain medium and the like.

The invention claimed is:

1. A fluid sensor measuring the composition and/or flow rate mixtures of water, oil and gas comprising:
   a core defining a fluid flow path;
   a confinement member located externally of the core, the core permits transmission of electromagnetic radiation at a frequency of the electromagnetic field; and
   a patch antenna located between the fluid flow path and the confinement member,
   wherein the confinement member confines an electromagnetic field which extends into the fluid flow path and the patch antenna couples an electrical signal to and/or from the electromagnetic field, and
   the confinement member comprises a composite material having one or more electrically conductive reinforcing elements embedded within a matrix and wherein the one or more reinforcing elements comprise carbon fibres.

2. The fluid sensor according to claim 1, wherein the electromagnetic field comprises a radio frequency (RF) electromagnetic field, a microwave field or a mm-wave field.

3. The fluid sensor according to claim 1, wherein the electromagnetic field has a frequency in the range, 1 kHz to 1 THz, 10 kHz to 100 GHz, 100 kHz to 10 GHz, or 1 MHZ to 1 GHz.

4. The fluid sensor according to claim 1, comprising an electrical source for generating an electrical signal in the form of at least one of an oscillator, a frequency source, a signal generator, a gain medium, and an amplifier.

5. The fluid sensor according to claim 1, comprising an electrical detector for detecting an electrical signal.

6. The fluid sensor according to claim 1, wherein the core comprises a PEEK material.

7. The fluid sensor according to claim 1, wherein the core comprises one or more glass fibres.

8. The fluid sensor according to claim 1, wherein the confinement member comprises an electrically conductive material.

9. The fluid sensor according to claim 1, wherein the matrix comprises a PEEK material.

10. The fluid sensor according to claim 1, wherein the patch antenna is located between the core and the confinement member.

11. The fluid sensor according to claim 1, wherein the patch antenna is at least partially embedded within the core.

12. The fluid sensor according to claim 1, wherein the patch antenna comprises an electrically conductive radiating element.

13. The fluid sensor according to claim 12, wherein the radiating element comprises a non-metallic electrically conductive material or substance.

14. The fluid sensor according to claim 12, wherein the radiating element comprises least one of electrically conductive elements, particles, fibres, sheets, and nanotubes.

15. The fluid sensor according to claims 12, wherein the radiating element comprises carbon.

16. The fluid sensor according to claims 12, wherein the radiating element comprises a metallic material or substance.

17. The fluid sensor according to claim 12, wherein the patch antenna comprises an electrically insulating substrate, the radiating element is defined on a first side of the substrate, and the patch antenna comprises an electrically conductive back plane defined on a second side of the substrate opposite to the first side of the substrate.

18. The fluid sensor according to claim 17, wherein the back plane is defined by the confinement member.

19. The fluid sensor according to claim 12, wherein the radiating element comprises at least a portion having a geometry selected from at least one of a triangle, a rectangular, a square, a circle, oval, ellipse.

20. The fluid sensor according to claim 12, wherein the radiating element comprises at least a portion that defines an elongate path.

21. The fluid sensor according to claim 20, wherein the path has at least one of a spiral a convoluted configuration.

22. The fluid sensor according to claim 1, comprising a further antenna.

23. The fluid sensor according to claim 1, comprising a plurality of further antennas.

24. The fluid sensor according to claim 1, comprising at least one further patch antenna.

25. A method for manufacturing a fluid sensor measuring the composition and/or flow rate of mixtures of water, oil, and gas comprising:
   providing a core defining a fluid flow path;
   providing a confinement member externally of the core; and
   providing a patch antenna between the fluid flow path and the confinement member,
   wherein the confinement member confines an electromagnetic field which extends into the fluid flow path and the patch antenna couples an electrical signal to and/or from the electromagnetic field, and embedding one or more electrically conductive reinforcing elements within a matrix of a composite material comprised within the confinement member, wherein the one or more reinforcing elements comprise carbon fibres.

26. The method according to claim 25, comprising forming the confinement member on or around the core.

27. The method according to claim 25, comprising forming the confinement member separately from the core and then locating the confinement member on or around the core.

28. The method according to claim 25, comprising forming the patch antenna on or around the core.

29. The method according to claim 25, comprising forming the patch antenna separately from the core and then locating the patch antenna on or around the core.

30. The method according to claim 25, comprising forming the confinement member on or around the patch antenna.

31. The method according to claim 25, comprising forming the confinement member separately from the patch antenna and then locating the confinement member on or around the patch antenna.

32. The method according to claim 25, comprising at least partially embedding the patch antenna within the core.

33. The method according to claim 25, comprising defining an electrically conductive radiating element of the patch antenna on a first side of an electrically insulating substrate of the patch antenna and defining an electrically conductive back plane of the patch antenna on a second side of the substrate opposite to the first side of the substrate.

34. The method according to claim 33, comprising:
forming the radiating element by coating, printing, painting or otherwise applying an electrically conductive substance to the substrate; and then
forming the patch antenna around the core.

35. The method according to claim 33, comprising:
forming the radiating element by coating, printing, painting or otherwise applying an electrically conductive substance to the core; and then
forming the substrate of the patch antenna on or around the radiating element.

36. The method according to claim 25, comprising using at least part of the core as an electrically insulating substrate of the patch antenna.

37. The method according to claim 25, comprising using the confinement member to define a back plane of the patch antenna.

* * * * *